(12) United States Patent
Goh et al.

(10) Patent No.: US 8,158,788 B2
(45) Date of Patent: Apr. 17, 2012

(54) METHOD FOR THE NITRATION OF 4,6-DIHYDROXY-2-METHYLPYRIMIDINE

(75) Inventors: Eun Mee Goh, Daejeon-si (KR); Jin Seuk Kim, Daejeon-si (KR); Jin Rai Cho, Daejeon-si (KR); Hyoun-Soo Kim, Daejeon-si (KR)

(73) Assignee: Agency for Defense Development, Daejeon-si (KR)

( * ) Notice: Subject to any disclaimer, the term of this patent is extended or adjusted under 35 U.S.C. 154(b) by 545 days.

(21) Appl. No.: 12/393,771

(22) Filed: Feb. 26, 2009

(65) Prior Publication Data

US 2010/0081811 A1    Apr. 1, 2010

(30) Foreign Application Priority Data

Sep. 30, 2008    (KR) .................. 10-2008-0096262

(51) Int. Cl.
*C07D 417/00*    (2006.01)

(52) U.S. Cl. ...................................................... 544/322
(58) Field of Classification Search ................... 544/322
See application file for complete search history.

(56) References Cited

OTHER PUBLICATIONS

Langlet et al., Propellants, Explosives & pyrotechnicss, 29 (2004), No. 6.*

* cited by examiner

*Primary Examiner* — Paul V. Ward
(74) *Attorney, Agent, or Firm* — Young & Thompson

(57) ABSTRACT

Disclosed is a method for the nitration of 4,6-dihydroxy-2-methylpyrimidine for the synthesis of 4,6-dihydroxy-5,5-dinitro-2-(dinitromethylene)-2,5-dihydropyrimidine which is used as a precursor of 1,1-diamino-2,2-dinitroethylene, one type of explosives. The present invention provides an improved method for the nitration of 4,6-dihydroxy-2-methylpyrimidine, wherein organic solvent is applied in the nitration process of 4,6-dihydroxy-2-methylpyrimidine thereby solving the safety problem while improving the yield of nitration.

20 Claims, 2 Drawing Sheets

METHOD FOR THE NITRATION OF 4,6-DIHYDROXY-2-METHYLPYRIMIDINE

TECHNICAL FIELD

The present invention relates to a method for the nitration of 4,6-dihydroxy-2-methylpyrimidine, which is used in the synthesis of 4,6-dihydroxy-5,5-dinitro-2-(dinitromethylene)-2,5-dihydropyrimidine which is used as a precursor of 1,1-diamino-2,2-dinitroethylene, a type of explosives. More specifically, the present invention relates to an improved method for the nitration of 4,6-dihydroxy-2-methylpyrimidine, wherein organic solvent is applied in the nitration of 4,6-dihydroxy-2-methylpyrimidine, thereby solving the safety problem while improving the yield of nitration.

BACKGROUND ARTS 4,6-dihydroxy-5,5-dinitro-2-(dinitromethylene)-2,5-dihydropyrimidine represented by the formula 2 is used as a precursor of 1,1-diamino-2,2-dinitroethylene, which is a type of explosives represented by the formula 3, and is synthesized by the nitration of 4,6-dihydroxy-2-methylpyrimidine represented by the formula 1.

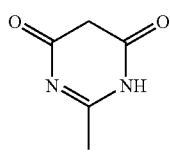

[Formula 1]

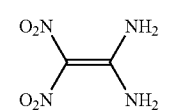

[Formula 2]

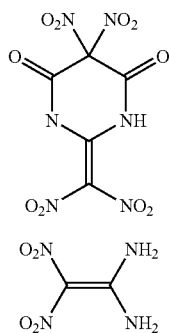

[Formula 3]

Describing the process in more detail, 4,6-dihydroxy-2-methylpyrimidine represented by the formula 1 is nitrated to give 4,6-dihydroxy-5,5-dinitro-2-(dinitromethylene)-2,5-dihydropyrimidine(precursor) represented by the formula 2, and then the precursor is hydrolyzed to give 1,1-diamino-2,2-dinitroethylene represented by the formula 3.

The nitration process of the 4,6-dihydroxy-2-methylpyrimidine is generally carried out by refluxing with concentrated sulfuric acid and concentrated nitric acid, and the most widely used method is the one proposed by A. A. Astrat'ev in Russian Journal of Organic Chemistry, Vol. 37, No. 5, 2001, p 729-733. In this method, firstly, 4,6-dihydroxy-2-methylpyrimidine is dissolved in a concentrated sulfuric acid at 15-20° C., the resulting solution is cooled to 5-10° C., and then nitric acid anhydride is slowly added to the solution while controlling the temperature to synthesize 4,6-dihydroxy-5,5-dinitro-2-(dinitromethylene)-2,5-dihydropyrimidine, as shown in the Reaction Scheme 1. The yield is reported to be about 75%.

[Reaction Scheme 1]

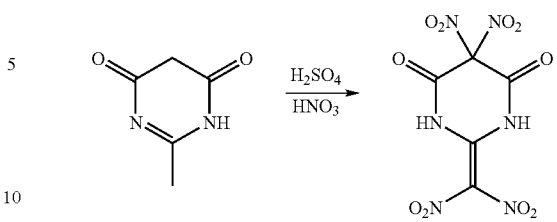

The conventional method as described above, however, has the disadvantage of generating excessive reaction heat in the process of adding nitric acid. In the process with the laboratory-scale of about 50 ml of reaction liquid, it is possible to collect reaction heat by setting the stirrer speed of above 500 rpm. In the process with scale of more than 1 L of reaction liquid, however, the time of adding nitric acid anhydride tends to become longer in order to control the temperature within a predetermined range due to the generation of an excessive heat of reaction, and there is a danger of explosion by the reaction heat when temperature control is not accurate enough.

SUMMARY OF THE INVENTION

The present invention has been designed to solve the problems of the conventional arts and has the objective of providing a method for the nitration of 4,6-dihydroxy-2-methylpyrimidine that is safe and enhance the yield of nitration. For this purpose, the present invention provides a method for the nitration of 4,6-dihydroxy-2-methylpyrimidine wherein organic solvent is applied in the process of the nitration.

DISCLOSURE OF THE INVENTION

Figure 1:
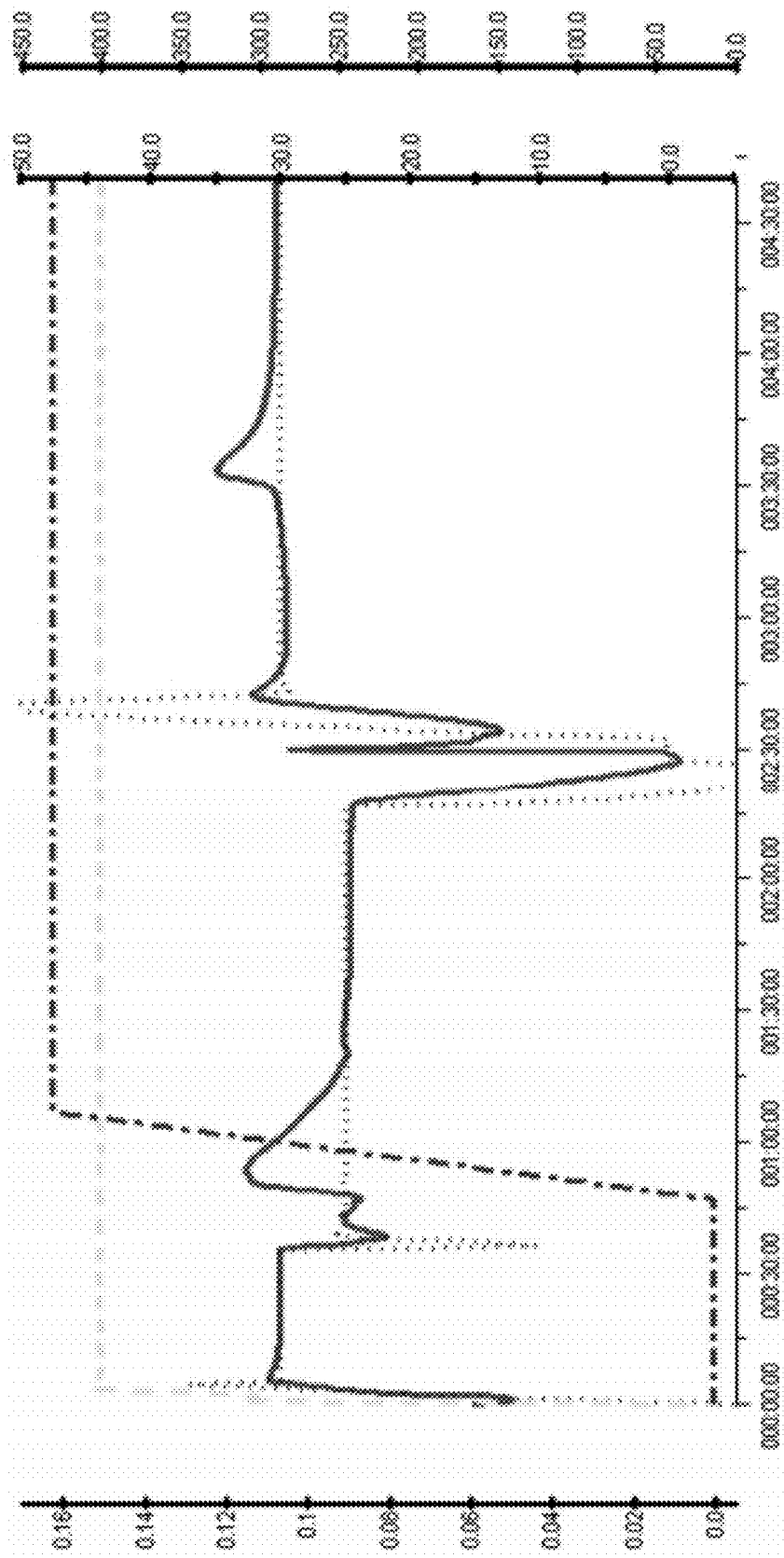
FIG. 1 is graphic view showing the change in the heat of reaction as concentrated nitric acid is added in the example 1.

The method for the nitration of 4,6-dihydroxy-2-methylpyrimidine according to the present invention comprise the steps of: (1) dissolving 4,6-dihydroxy-2-methylpyrimidine in a concentrated sulfuric acid; (2) adding halogenated organic solvent to the solution obtained by step (1); and (3) adding concentrated nitric acid to the solution obtained by step (2) and stirring the solution.

The method for the nitration of 4,6-dihydroxy-2-methylpyrimidine of the present invention can be represented as in the Reaction Scheme 2.

[Reaction Scheme 2]

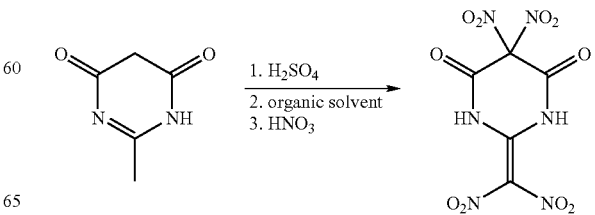

The concentrated sulfuric acid used in step (1) has preferably concentration of 95-98% and the 4,6-dihydroxy-2-methylpyrimidine has preferably 95% or more of purity.

In the step (1), it is preferable to dissolve 4,6-dihydroxy-2-methylpyrimidine in the concentrated sulfuric acid while stirring the solution for 30 minutes so that 4,6-dihydroxy-2-methylpyrimidine is sufficiently dissolved considering the large initial reaction heat of the nitration process. The temperature for dissolving 4,6-dihydroxy-2-methylpyrimidine in the concentrated sulfuric acid is not specifically limited, but around room temperature is preferable. The temperature of the reactor, if not externally controlled, rises to above 60° C. during the dissolution and then decreases to the room temperature. The equivalent ratio of 4,6-dihydroxy-2-methylpyrimidine and the concentrated sulfuric acid in the obtained solution is preferably 4,6-dihydroxy-2-methylpyrimidine: concentrated sulfuric acid=1:6-8, and more preferably 1:7. If the equivalent of the concentrated sulfuric acid is less than 6, the yield of nitration process decreases, which is not preferable, and if the equivalent of the concentrated sulfuric acid is more than 8, the amount of the waste concentrated sulfuric acid increases, which also is not preferable.

The halogenated organic solvent used in step (2) should be a solvent that is not nitrated in the mixed acid, and can be one or more selected from dichloromethane, chloroform, carbon tetrachloride, 1,2-dichloroethane, trichloroethylene, dibromomethane, bromochloromethane, bromoform and 1,2-dibromoethane. The amount of use of the organic solvent, calculated by the volume ratio with respect to the solution obtained in the step (1), is preferably the volume ratio of the solution obtained in the step (1): halogenated organic solvent=1:0.5-1.5. If the ratio of use of the organic solvent is less than 0.5, the effect of using the organic solvent is very little which is not preferable and if the ratio of use of the organic solvent is more than 1.5, the cost of reactor and utility is increased due to the increased total volume by the organic solvent, which also is not preferable.

The concentrated nitric acid used in step (3) has preferably concentration of above 98%, and the amount of use of the concentrated nitric acid is preferably the weight ratio of the solution obtained in the step (2): concentrated nitric acid=1: 0.8-1.2. If the ratio of use of the concentrated nitric acid is less than 0.8, the yield of reaction is decreased and if more than 1.2, too much nitric fume is generated after the reaction and there is little enhancement of yield and is not preferable.

In the step (3), the time of adding the concentrated nitric acid depends on the type of the organic solvent, but is preferably from 3 minutes to 1 hour, or more preferably, 15-30 minutes. When the time is less than 3 minutes, reaction may not be sufficiently completed, and when the time is more than 1 hour, the delay of time can cause problems in the reaction process and there is a danger of self explosion due to the interaction of 4,6-dihydroxy-5,5-dinitro-2-(dinitromethylene)-2,5-dihydropyrimidine, a reaction intermediate before the hydrolysis, and water in the mixed acid.

The temperature of reaction in step (3) is preferably 10° C.-40° C. When the temperature is lower than 10° C., there is the problem of increasing the time for synthesis and when the temperature is higher than 40° C., there is also the problem of difficulty in controlling the reaction velocity.

After adding concentrated nitric acid as described above, the reaction is completed by stirring 1-5 hours. When the time of stirring is less than 1 hour, the yield of reaction decreases, and when the time exceeds 5 hours, there is a danger of explosion of dinitromethane produced during hydrolysis, which is not preferable.

The 4,6-dihydroxy-5,5-dinitro-2-(dinitromethylene)-2,5-dihydropyrimidine is obtained as a yellow solid at a little wet state with the yield of about 85%, and then it can be hydrolyzed without further refining to provide 1,1-diamino-2,2-dinitroethylene.

[Preferred Embodiment of the Invention]

The present invention will be described in more detail with reference to specific example. The example, however, is for illustration of the present invention and should not be deemed to limit the scope of the invention.

EXAMPLE 1

Nitration is carried out with the material and amount shown in the Table 1.

TABLE 1

| Reagent used | Mole | Amount | Equivalent |
|---|---|---|---|
| 4,6-Dihydroxy-2-methylpyrimidine | 0.75 | 95 g | 1 |
| Concentrated sulfuric acid (95%) | 5.35 | 285 ml (524.4 g) | 7.13 |
| Concentrated nitric acid (98%) | 5.09 | 321 g | 6.79 |
| Dichloromethane | 2 | 250 ml | 3.73 |

First, sulfuric acid (95%, 524.4 g) was introduced into a reactor (2 L) with jacket temperature 25° C., and 4,6-dihydroxy-2-methylpyrimidine (95 g) was added and dissolved for 30 minutes with stirrer speed of 300 rpm. 250 ml of dichloromethane was added at the same temperature, and then nitric acid (98%, 321 g) was added. After completing the addition of nitric acid, the same temperature was maintained until the nitration process was completed.

In the above process, enhanced fluidity has been obtained by using dichloromethane, a halogenated organic solvent, in the nitration reaction, and difference between the internal temperature of the reactor and the temperature of the reactor jacket didn't exceed 10° C. The generation of heat of reaction as the nitric acid was introduced in this example is shown in FIG. 1. As can be seen from the graph of FIG. 1, where the heat of reaction is represented by bold solid line and the amount of introduced nitric acid by the dotted line, the change of heat of reaction is not large, which can be interpreted that the heat of reaction is absorbed as latent heat of vaporization of dichloromethane. No more heat of reaction was observed at 15 minutes after the completion of adding nitric acid. The temperature of the reactor became same with that of the jacket, indicating that heat of reaction was not generated any more. The temperature of the reactor was maintained for 45 minutes for stabilization, and the nitration reaction was completed.

The 4,6-dihydroxy-5,5-dinitro-2-(dinitromethylene)-2,5-dihydropyrimidine produced by the nitration reaction of 4,6-dihydroxy-2-methylpyrimidine in this example was hydrolyzed to give 1,1-diamino-2,2-dinitroethylene with the combined yield of 85%.

COMPARATIVE EXAMPLE 1

The nitration of 4,6-dihydroxy-2-methylpyrimidine was carried out as in the example 1 except that the temperature of the reactor jacket was lowered to −7° C. and 500 g of nitric acid was used without adding dichloromethane.

Sulfuric acid (95%, 524.4 g) was introduced into the 2 L reactor with jacket temperature of −7° C., and 4,6-dihydroxy-2-methylpyrimidine (95 g) was added and dissolved for 30 minutes with stirrer speed of 300 rpm. The 4,6-dihydroxy-2- methylpyrimidine was not sufficiently dissolved in the sulfuric acid, and after the internal temperature of the reactor was lowered to 5° C. while maintaining the ideal solution, nitric acid was introduced with velocity of 10 g/min. But as the internal temperature of the reactor increased above 20° C. at the early stage of introducing nitric acid, supplying nitric acid was stopped, and resumed with decreased introduction velocity of 5 g/min after the temperature of the reactor was lowered to 5° C. thereby stabilizing the reactor temperature around 6° C. The amount of used nitric acid was 500 g (7.93 mol), and the reactor jacket temperature was maintained at about −7° C. After the completion of addition of nitric acid, the temperature of the reactor was stabilized at around 0° C., and the temperature of the reactor jacket at around −10° C. Although the temperature of the reactor has been stabilized until the completion of the reaction, the problem was in the state of the stirrer and the slurry state of the reaction solution. As the reaction went on, reaction slurry was not sufficiently mixed by the propeller-type stirrer, and as the result, only the reaction solution in the lower part of the reactor was mixed with unmixed slurry stacking on the upper part of the reactor. The problem became more serious as reaction proceeded.

After confirmed that there was no more reaction heat, the reaction was completed, the internal temperature of the reactor was lowered, and the resultant was discharged from the reactor. But the outlet of the reactor was so small that the slurry was discharged very little. Risking some danger of the process, the temperature of the reactor had to be further lowered, enough water was introduced, and the slurry was dissolved by the water and discharged.

Figure 2:
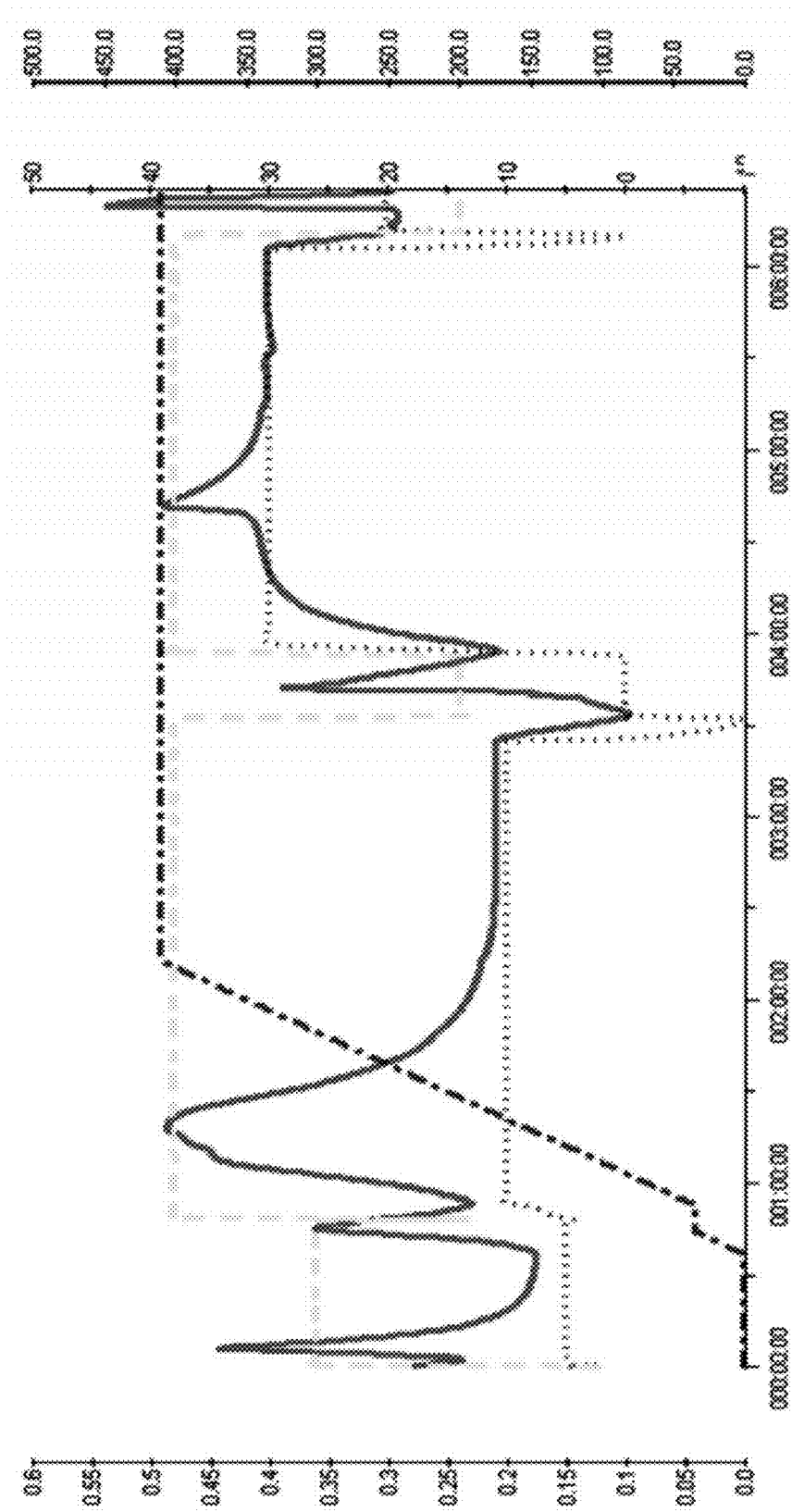
FIG. 2 is graphic view showing the change in the heat of reaction as concentrated nitric acid is added in the comparative example 1.

The generation of heat of reaction as the nitric acid was introduced in this comparative example is shown in FIG. 2. As in FIG. 1, the heat of reaction is represented by bold solid line and the amount of introduced nitric acid by the dotted line. The reaction could not be carried out at room temperature due to the absence of organic solvent and the reaction had to be carried out at very low temperature. As can be seen in the FIG. 2, the heat of reaction largely varied compared to FIG. 1 as nitric acid was introduced.

The 4,6-dihydroxy-5,5-dinitro-2-(dinitromethylene)-2,5-dihydropyrimidine produced by the nitration reaction of 4,6-dihydroxy-2-methylpyrimidine in this comparative example, was hydrolyzed to give 1,1-diamino-2,2-dinitroethylene with the combined yield of 50%.

COMPARATIVE EXAMPLE 2

The nitration of 4,6-dihydroxy-2-methylpyrimidine was carried out as in the example 1 except that the temperature of the reactor jacket was set to 5° C. and 500 g of nitric acid was used without adding dichloromethane.

Nitric acid was introduced as slowly as possible in order to minimize the generation of reaction heat and to keep reaction temperature constantly. After 50 g of nitric acid was added, the temperature of the reactor jacket was raised to 10° C. and maintained at the same temperature till the reaction completed. The temperature of the reactor was increased up to 39° C., and the time for the nitration reaction was 3.5 hours.

The 4,6-dihydroxy-5,5-dinitro-2-(dinitromethylene)-2,5-dihydropyrimidine produced by the nitration reaction of 4,6-dihydroxy-2-methylpyrimidine in this comparative example was hydrolyzed to give 1,1-diamino-2,2-dinitroethylene with the combined yield of 70%.

[Industrial Applicability]

By using the method for the nitration of 4,6-dihydroxy-2-methylpyrimidine according to the present invention, the temperature is easily controlled and the nitration process is carried out safely since reaction heat is not generated rapidly, and 4,6-dihydroxy-5,5-dinitro-2-(dinitromethylene)-2,5-dihydropyrimidine can be produced with high yield in shortened time.

What is claimed is:

1. A method for the nitration of 4,6-dihydroxy-2-methylpyrimidine comprising the steps of:
    (1) dissolving 4,6-dihydroxy-2-methylpyrimidine in concentrated sulfuric acid to form a solution of the 4,6-dihydroxy-2-methylpyrimidine;
    (2) adding halogenated organic solvent to the 4,6-dihydroxy-2-methylpyrimidine solution obtained from the above step (1) to form a mixed solution of the 4,6-dihydroxy-2-methylpyrimidine solution and the halogenated organic solvent; and
    (3) adding concentrated nitric acid to the mixed solution obtained from the above step (2) and stirring the solution to form a 4,6-dihydroxy-5,5-dinitro-2-(dinitromethylene)-2,5-dihydropyrimidine.

2. The method according to claim 1, wherein the halogenated organic solvent is at least one selected from the group consisting of dichloromethane, chloroform, carbon tetrachloride, 1,2-dichloroethane, trichloroethylene, dibromomethane, bromochloromethane, bromoform and 1,2-dibromoethane.

3. The method according to claim 1, wherein the concentrated sulfuric acid has a concentration of 95-98% and the 4,6-dihydroxy-2-methylpyrimidine has 95% or more purity.

4. The method according to claim 1, further comprising in the step (1), the 4,6-dihydroxy-2-methylpyrimidine in the concentrated sulfuric acid is for 30 minutes.

5. The method according to claim 4, wherein a temperature of the solution obtained from the step (1) rises above 60° C. during the dissolving and then decreases to a room temperature.

6. The method according to claim 1, wherein a ratio between the 4,6-dihydroxy-2-methylpyrimidine and the concentrated sulfuric acid in the solution is from 1:6 to 1:8.

7. The method according to claim 1, wherein a ratio between the 4,6-dihydroxy-2-methylpyrimidine and the concentrated sulfuric acid in the solution is 1:7.

8. The method according to claim 1, wherein a volume ratio of the solution obtained from the step (1) and the halogenated organic solvent is from 1:0.5 to 1:1.5.

9. The method according to claim 1, wherein the concentrated nitric acid has a concentration of 98% or more.

10. The method according to claim 1, wherein a weight ratio of the solution obtained from the step (2) and the concentrated nitric acid is from 1:0.8 to 1:2.

11. The method according to claim 1, further comprising in the step (3), adding the concentrated nitric acid to the mixed solution obtained from the step (2) for 30 minutes to 1 hour.

12. The method according to claim 1, further comprising in the step (3), adding the concentrated nitric acid to the mixed solution obtained from the step (2) for 15 to 30 minutes.

13. The method according to claim 11, wherein a temperature of the solution obtained from the step (3) is from 10° C. to 40° C.

14. The method according to claim 1, further comprising in the step (3), stirring the solution for 1 to 5 hours.

15. A method for the nitration of 4,6-dihydroxy-2-methylpyrimidine comprising the steps of:
    (1) dissolving 4,6-dihydroxy-2-methylpyrimidine in concentrated sulfuric acid to form a solution of the 4,6-dihydroxy-2-methylpyrimidine;
    (2) adding halogenated organic solvent to the 4,6-dihydroxy-2-methylpyrimidine solution obtained from the above step (1) to form a mixed solution of the 4,6-dihydroxy-2-methylpyrimidine solution and the halogenated organic solvent; and (3) adding concentrated nitric acid to the mixed solution obtained from the above step (2) and stirring the solution to form a 4,6-dihydroxy-5,5-dinitro-2-(dinitromethylene)-2,5-dihydropyrimidine, wherein, the halogenated organic solvent is at least one selected from the group consisting of dichloromethane, chloroform, carbon tetrachloride, 1,2-dichloroethane, trichloroethylene, dibromomethane, bromochloromethane, bromoform and 1,2-dibromoethane.

16. The method according to claim 15, wherein the concentrated sulfuric acid has a concentration of 95-98% and the 4,6-dihydroxy-2-methylpyrimidine has 95% or more purity.

17. The method according to claim 15, further comprising in the step (1), the 4,6-dihydroxy-2-methylpyrimidine in the concentrated sulfuric acid is for 30 minutes.

18. The method according to claim 17, wherein a temperature of the solution obtained from the step (1) rises above 60° C. during the dissolving and then decreases to a room temperature.

19. The method according to claim 15, wherein a ratio between the 4,6-dihydroxy-2-methylpyrimidine and the concentrated sulfuric acid in the solution is from 1:6 to 1:8.

20. The method according to claim 15, wherein a ratio between the 4,6-dihydroxy-2-methylpyrimidine and the concentrated sulfuric acid in the solution is 1:7.

* * * * *